(12) United States Patent
Roh et al.

(10) Patent No.: US 10,760,256 B2
(45) Date of Patent: Sep. 1, 2020

(54) AIR TREATMENT DEVICE (71) Applicant: Tae Sik Roh, Jeju-Do (KR)

(72) Inventors: Ji Nyeong Roh, Seoul (KR); Tae Sik Roh, Busan (KR)

(73) Assignee: Tae Sik Roh, Jeju-Do (KR)

( * ) Notice: Subject to any disclaimer, the term of this patent is extended or adjusted under 35 U.S.C. 154(b) by 431 days.

(21) Appl. No.: 14/766,736

(22) PCT Filed: Feb. 6, 2014

(86) PCT No.: PCT/KR2014/001037
§ 371 (c)(1),
(2) Date: Aug. 7, 2015

(87) PCT Pub. No.: WO2014/123377
PCT Pub. Date: Aug. 14, 2014

(65) Prior Publication Data
US 2015/0376885 A1 Dec. 31, 2015

(30) Foreign Application Priority Data

Feb. 7, 2013 (KR) .................. 10-2013-0013895

(51) Int. Cl.
*E03D 9/04* (2006.01)
*A61L 9/00* (2006.01)
*E03D 9/052* (2006.01)

(52) U.S. Cl.
CPC .................. *E03D 9/04* (2013.01); *A61L 9/00* (2013.01); *E03D 9/052* (2013.01)

(58) Field of Classification Search
CPC .............. A61L 9/00; E03D 9/04; E03D 9/052
(Continued)

(56) References Cited

U.S. PATENT DOCUMENTS 3,790,970 A * 2/1974 Bendersky ............. E03D 9/052
 200/85 A
4,166,298 A * 9/1979 Pearson .................. E03D 9/052
 4/213
(Continued)

FOREIGN PATENT DOCUMENTS

JP 10-096253 A 4/1998
JP 2012-207488 A 10/2012
(Continued)

OTHER PUBLICATIONS

KR-20130002392-A Machine Translation (Year: 2013).*
(Continued)

*Primary Examiner* — David P Angwin
*Assistant Examiner* — William R Klotz
(74) *Attorney, Agent, or Firm* — The PL Law Group, PLLC (57) ABSTRACT

An air treatment device is disclosed. The air treatment device according to one embodiment of the present invention comprises: a first air passage part of which one side is connected with at least one contamination space; a first air suction part for enabling the contaminated air within the contamination space to flow into the first air passage part; and a first air treatment part including: a partition formed inside a toilet water tank; at least one of through-holes, which is formed in the partition, connected with the other side of the first air passage part, and connected with a space inside the partition; and an air discharging part for discharging the contaminated air into the inside of the partition.

6 Claims, 4 Drawing Sheets

(58) Field of Classification Search
USPC .................................... 4/209 R, 209 FF, 218
See application file for complete search history.

(56) References Cited

U.S. PATENT DOCUMENTS

| | | | | |
|---|---|---|---|---|
| 4,232,406 | A | * | 11/1980 | Beeghly ............... E03D 9/052 4/213 |
| 4,251,888 | A | * | 2/1981 | Turner ................ E03D 9/052 4/213 |
| 4,318,192 | A | * | 3/1982 | Williams ............. E03D 9/052 4/213 |
| 4,590,629 | A | | 5/1986 | Lusk |
| 4,864,664 | A | * | 9/1989 | Higgins ............... E03D 9/052 4/213 |
| 5,010,600 | A | * | 4/1991 | Prisco ................. E03D 9/052 4/211 |
| 5,321,856 | A | * | 6/1994 | Gastesi ................ E03D 9/05 4/213 |
| 5,361,422 | A | * | 11/1994 | Vincent ............... E03D 9/05 4/213 |
| 5,369,813 | A | * | 12/1994 | Goddard ............. E03D 9/052 4/213 |
| 5,519,899 | A | * | 5/1996 | Taylor ................. E03D 3/10 4/213 |
| 5,718,005 | A | * | 2/1998 | Ng ...................... E03D 9/05 4/213 |
| 5,727,262 | A | * | 3/1998 | Littlejohn ............ E03D 9/052 4/213 |
| 6,202,226 | B1 | * | 3/2001 | Shoptaugh ........... E03D 9/05 4/209 R |
| 2002/0194670 | A1 | * | 12/2002 | Hashemi ............. A63B 33/002 2/452 |
| 2008/0307570 | A1 | | 12/2008 | Marks |
| 2009/0056007 | A1 | * | 3/2009 | Pham .................. E03L 39/052 4/347 |
| 2010/0088813 | A1 | * | 4/2010 | Onishi ................. E03D 3/10 4/347 |
| 2013/0086736 | A1 | * | 4/2013 | Larouche ............ E03D 9/052 4/348 |

FOREIGN PATENT DOCUMENTS

| | | | |
|---|---|---|---|
| KR | 10-2004-0020232 A | | 3/2004 |
| KR | 20040020232 A | * | 3/2004 |
| KR | 10-2013-0002392 A | | 1/2013 |
| KR | 20130002392 A | * | 1/2013 |

OTHER PUBLICATIONS

KR-20040020232-A Machine Translation (Year: 2004).*
International Search Report for PCT/KR2014/001037.
Written Opinion of the International Search Authority for PCT/KR2014/001037.
Office action dated Apr. 30, 2019 from India Patent Office in a counterpart India Patent Application No. 2484/KOLNP/2015 (all the cited references are listed in this IDS.) (English translation is also submitted herewith.).

* cited by examiner

AIR TREATMENT DEVICE

TECHNICAL FIELD

The present invention relates to an air treatment device, and more particularly, to an air treatment device using a water tank of a toilet.

BACKGROUND ART

Generally, a ventilator is installed at a bathroom to ventilate an inside of the bathroom. However, even through the ventilator is operated, only internal air of the bathroom may be ventilated, but internal air in a toilet hole of a toilet may not be ventilated. Even when a user flushes the toilet after going to the bathroom, odor and germs remain and proliferate in a space inside the toilet hole. At this time, the odor and the germs inside the toilet hole spread throughout the bathroom, and contaminate air inside the bathroom. Also, the odor and the germs inside the toilet hole may spread not only throughout the bathroom, but also throughout the house, and may contaminate air throughout the house. This may cause an internal environment of the house to become unsanitary, and the old and weak or children may be infected by pathogenic bacteria.

Meanwhile, in the case of apartment houses, passages of the ventilators are connected with each other among the apartment houses, and thus when the ventilator is not operated, contaminated air may be introduced from an adjacent house into an inside through the ventilator.

PRIOR ART DOCUMENTS

Korean U.M. Registration No. 20-0262167 (Mar. 18, 2002)

DISCLOSURE

Technical Problem

The present invention is directed to providing an air treatment device which is capable of treating contaminated air in a contamination space such as a toilet hole.

Also, the present invention is directed to providing an air treatment device which is capable of removing foreign substances contained in air and then discharging the air into a room.

Technical Solution

One aspect of the present invention provides an air treatment device including a first air passage part of which one side is connected with at least one contamination space; a first air suction part configured to introduce contaminated air in the contamination space into the first air passage part; and a first air treatment part including a partition formed in a toilet water tank, at least one through-hole formed in the partition, connected with the other side of the first air passage part, and being in communication with a space inside the partition, and an air discharging part configured to discharge the contaminated air into an inside of the partition.

A plurality of through-holes may be formed along the air discharging part from an upper end of the air discharging part to a lower end thereof.

A water level of cleaning water in the toilet water tank may be controlled according to a contamination level in the contamination space.

The device may further include a second air passage part of which one side is connected with the space inside the partition, and the other side is connected with the first external space, and a second air suction part configured to introduce the contaminated air inside the partition into the second air passage part.

The second air suction part may control suction intensity according to an amount of the contaminated air discharged inside the partition or a water level of cleaning water in the toilet water tank.

The partition may include an upper plate formed in the toilet water tank, and a side plate formed downward from an end of the upper plate and also formed so that an end thereof is spaced a predetermined distance from a lower surface of the toilet water tank.

A lower end of the partition may be formed lower than a minimum water level of the cleaning water in the toilet water tank.

The contamination space may be at least one of a toilet hole in a toilet, a bathroom, a kitchen, a living room, a veranda, a smoking room, a resting room, a garbage storage place, an office, a laboratory, a reading room, and a place having a lower oxygen concentration than a predetermined reference value.

The device may further include a second air treatment part formed in the toilet water tank to be spaced from the first air treatment part; a third air passage part of which one side is connected with the second external space, and the other side is connected with an air discharging part of the second air treatment part; a third air suction part configured to introduce air of the second external space into the third air passage; a fourth air passage part of which one side is connected with a partition of the second air treatment part, and the other side is connected with an indoor space; and a fourth air suction part configured to enable the air inside the partition of the second air treatment part to introduce into the fourth air passage part.

The third air suction part may filter the air of the second external space introduced through the third air passage part, and then may introduce the air into the second air treatment part.

Advantageous Effects

According to the embodiment of the present invention, since the contaminated air in the contamination space is treated using the toilet water tank, the cleaning water in the toilet water tank in which the contaminated air is dissolved is naturally discharged to the toilet tank, and then replaced with new cleaning water, and thus the contaminated air in the contamination space can be easily treated. Also, since the contaminated air in the contamination space is discharged to the external space or the toilet tank in the state in which the air treatment device is shut off from the outside, the contaminated air can be prevented from being introduced from the outside into the room. Furthermore, it is possible to remove the foreign substances, such as dust and yellow dust, contained in the external air and then to discharge fresh air from which the foreign substances are removed.

MODES OF THE INVENTION

Hereinafter, an air treatment device of the present invention will be described in detail with reference to FIGS. 1 to 6. However, these are only the exemplary embodiments, and the present invention is not limited thereto.

In the following description, detailed descriptions of well-known functions or constructions will be omitted since they would obscure the invention in unnecessary detail. Also, the terms used herein are defined according to the functions of the present invention. Thus, the terms may vary depending on user's or operator's intentions or practices. Therefore, the terms used herein must be understood based on the descriptions made herein.

The technical spirit of the present invention is determined by the claims, and the following embodiments are provided to merely explain the technical spirit of the present invention to those skilled in the art to which the present invention pertains.

Figure 1:
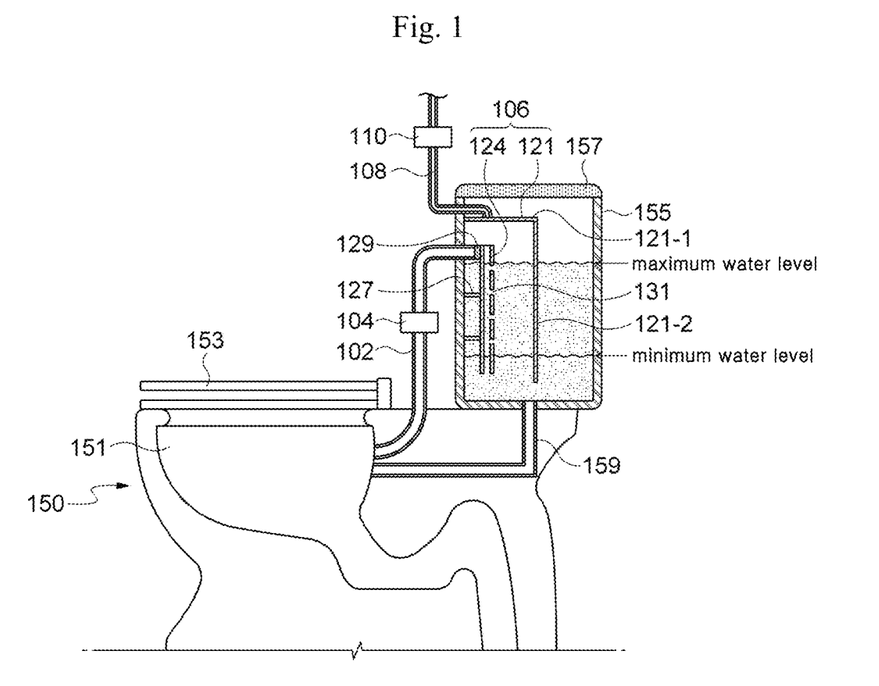
FIG. 1 is a view illustrating an air treatment device according to one embodiment of the present invention.

FIG. 1 is a view illustrating an air treatment device according to one embodiment of the present invention.

Referring to FIG. 1, the air treatment device 100 includes a first air passage part 102, a first air suction part 104, an air treatment part 106, a second air passage part 108, and a second air suction part 110.

One side of the first air passage part 102 is connected with a contamination space, and the other side thereof is connected with the air treatment part 106. For example, the first air passage part 102 may be a duct, a pipe, a hose, or the like, but the present invention is not limited thereto. The first air passage part 102 may be configured with various other tools through which air flows.

Here, the contamination space is an area in which the air is contaminated by odor and various germs or the like. For example, the contamination space may be a toilet 150 in a bathroom. At this time, the one side of the first air passage part 102 may be connected with a toilet hole 151. A toilet cover 153 may be provided at an upper portion of the toilet hole 151. Here, when the toilet cover 153 is opened, contaminated air in the toilet hole 151 spreads throughout the bathroom and contaminates air throughout the bathroom. At this time, the contaminated air gradually spreads to an outside of the bathroom, and contaminates air throughout a house. When the toilet cover 153 is closed, the odor and various germs gradually proliferate in the toilet hole 151, and serve as a contamination source which contaminates air throughout the house.

The first air suction part 104 serves to suck the contaminated air in the toilet hole 151 and to introduce the contaminated air into the first air passage part 102. For example, the first air suction part 104 may include a suction fan which sucks air. At this time, at least one first air suction part 104 may be installed in the first air passage part 102, but the present invention is not limited thereto. The first air suction part 104 may include a pump which further strongly sucks the contaminated air in the toilet hole 151. Suction intensity of the first air suction part 104 may be controlled according to a contamination level in the toilet hole 151 (i.e., the contamination space).

The air treatment part 106 is formed in a toilet water tank 155 of the toilet 150. Cleaning water is stored in the toilet water tank 155. A water tank cover 157 is provided at an upper end of the toilet water tank 155 to open and close the toilet water tank 155. The toilet water tank 155 is in communication with the toilet hole 151 through a connection passage 159. The cleaning water in the toilet water tank 155 is discharged to the toilet hole 151 depending on a user's operation.

Figure 2:
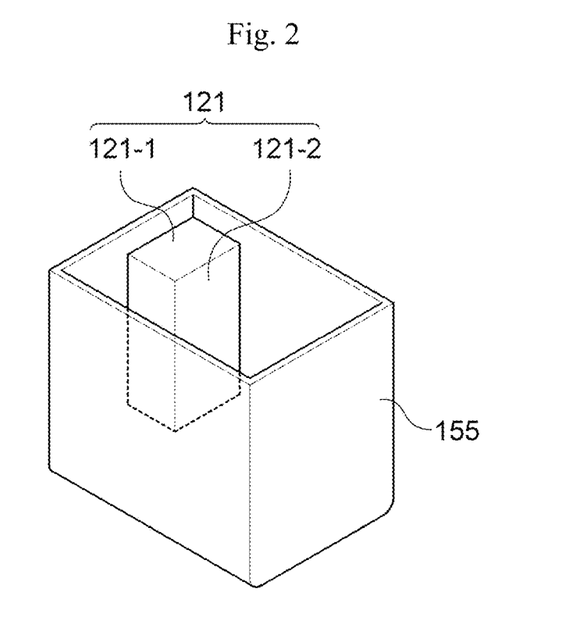
FIG. 2 is a view illustrating a state in which an air treatment part is formed in a toilet water tank according to one embodiment of the present invention.

FIG. 2 is a view illustrating a state in which the air treatment part is formed in the toilet water tank according to one embodiment of the present invention. Referring to FIGS. 1 and 2, the air treatment part 106 may be formed at an edge portion of the toilet water tank 155. However, a position of the air treatment part 106 is not limited thereto.

The air treatment part 106 includes a partition 121 and an air discharging part 124. The partition 121 is installed and fixed to an inner wall of the toilet water tank 155. The partition 121 includes an upper plate 121-1 and a side plate 121-2. The upper plate 121-1 may be fixed to the inner wall of the toilet water tank 155 at the upper end of the toilet water tank 155. The side plate 121-2 may be formed to extend downward from an end of the upper plate 121-1.

Here, an end of the side plate 121-2 is formed to be spaced a predetermined distance from a lower surface of the toilet water tank 155. A lower end of the partition 121 is formed to be opened. That is, the partition 121 is formed to be in communication with an internal space of the toilet water tank 155. In this case, the cleaning water of the toilet water tank 155 is also introduced into an inside of the partition.

At this time, the end of the side plate 121-2 is formed lower than a minimum water level of the cleaning water in the toilet water tank 155. That is, the end of the side plate 121-2 is formed to be submerged into the cleaning water, when the cleaning water in the toilet water tank 155 is located at the minimum water level. Here, the minimum water level of the cleaning water in the toilet water tank 155 is a water level when the cleaning water in the toilet water tank 155 is discharged to the toilet hole 151. In this case, air inside the partition 121 is always isolated from air in the toilet water tank 155.

The air treatment part 106 has an independent space in the toilet water tank 155 defined by the partition 121. Here, the partition 121 is illustrated to have a quadrangular pillar shape. However, a shape of the partition 121 is not limited thereto, and may have various other shapes. The partition 121 may be integrally formed with the toilet water tank 155, but the present invention is not limited thereto. The partition 121 may be manufactured separately from the toilet water tank 155, and then may be coupled in the toilet water tank 155.

The air discharging part 124 is formed inside the partition 121. The air discharging part 124 may be formed in a depthwise direction of the toilet water tank 155. The air discharging part 124 may be fixed to an inside of the toilet water tank 155 through a fixing part 127. One side of the air discharging part 124 is connected with the other side of the first air passage part 102. At this time, the one side of the air discharging part 124 is connected with the other side of the first air passage part 102 through a connection part 129.

An inside of the air discharging part 124 is formed to be hollow. In this case, the cleaning water is also introduced into the inside of the air discharging part 124. At least one through-hole 131 may be formed at the air discharging part 124. A plurality of through-holes 131 may be formed along the air discharging part 124 from an upper end of the air discharging part 124 to a lower end thereof to be spaced at regular intervals. The intervals among the through-holes 131 may be formed constantly, but the present invention is not limited thereto. Also, sizes of the through-holes 131 may be formed to be the same as or different from each other. At least one through-hole 131 may be formed higher than a maximum water level of the cleaning water in the toilet water tank 155. The air discharging part 124 serves to discharge the contaminated air introduced from the first air passage part 102 to the inside of the toilet water tank 155. Specifically, the contaminated air introduced into the air discharging part 124 through the first air passage part 102 may be dissolved in the cleaning water in the toilet water tank 155 or may be discharged to an outside through the second air passage part 108. Description thereof will be given later with reference to FIGS. 3 and 4.

Referring to FIG. 1 again, one side of the second air passage part 108 is connected with the air treatment part 106, and the other side of the second air passage part 108 is connected with an external space. Here, the external space may be an outside of the house (e.g., a rooftop or the like), but the present invention is not limited thereto. The external space may be an internal space of a tool for discharging night soil or the like, such as a drain. For example, the second air passage part 108 may be a duct, a pipe, a hose or the like, but the present invention is not limited thereto. Various other tools through which the air flows may be used as the second air passage part 108.

The second air suction part 110 serves to suck the contaminated air in the air treatment part 106, and to introduce the contaminated air into the second air passage part 108. For example, the second air suction part 110 may include a suction fan which sucks the air. At this time, at least second air suction part 110 may be installed in the second air passage part 108, but the present invention is not limited thereto. The second air suction part 110 may include a pump which further strongly sucks the contaminated air in the air treatment part 106. When the pumps are used as the first and second air suction parts 104 and 110, the first and second air suction parts 104 and 110 may be integrally formed.

Figure 3:
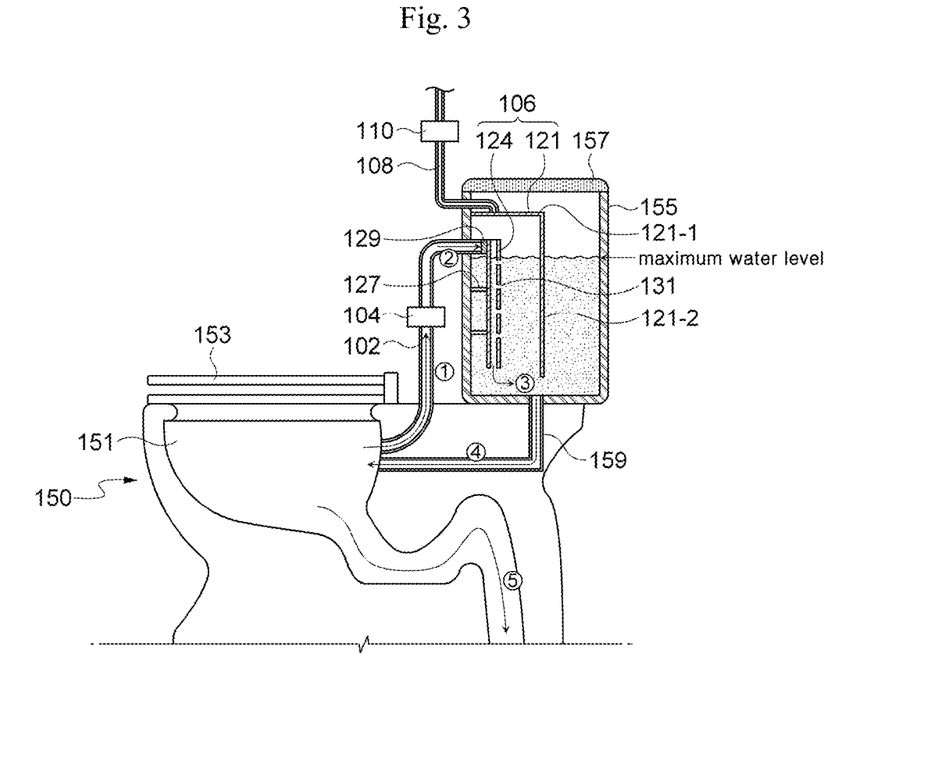
FIG. 3 is a view illustrating a process in which contaminated air in a toilet hole is discharged to an outside, when cleaning water in a toilet water tank reaches a maximum water level, in the air treatment device according to one embodiment of the present invention.

FIG. 3 is a view illustrating a process in which the contaminated air in the toilet hole is discharged to an outside, when the cleaning water in the toilet water tank reaches the maximum water level, in the air treatment device according to one embodiment of the present invention. Here, the maximum water level is a water level when the cleaning water in the toilet water tank is supplied and rising again.

Referring to FIG. 3, the contaminated air in the toilet hole 151 is introduced into the first air passage part 102 through the first air suction part 104 (①). Then the contaminated air introduced into the first air passage part 102 flows along the first air passage part 102, and then is introduced into the air discharging part 124 (②). Here, when the cleaning water in the toilet water tank 155 is located at the maximum water level, most of the air discharging part 124 is submerged in the cleaning water. When the first air suction part 104 strongly sucks the contaminated air in the toilet hole 151, the contaminated air is spurted from one side of the air discharging part 124, and dissolved in the cleaning water in the air discharging part 124 (③). And the cleaning water in the toilet water tank 155, in which the contaminated air is dissolved, is discharged into the toilet hole 151 through the connection passage 159 according to the user's operation (④). Then, the cleaning water in the toilet hole 151 is discharged to a toilet tank (not shown) according to the user's operation (⑤).

Here, the cleaning water in the toilet water tank 155 is gradually contaminated, as the contaminated air is dissolved therein. However, as a user repeatedly uses the toilet 150, the cleaning water in the toilet water tank 155 is repeatedly discharged to the toilet hole 151, and naturally replaced with new cleaning water. Therefore, the cleaning water in the toilet water tank 155 is not needed to be replaced artificially. Also, as the user repeatedly uses the toilet 150, the cleaning water in which the contaminated air in the toilet hole 151 is dissolved is repeatedly discharged to the toilet tank (not shown), and thus the air in the bathroom may be maintained hygienically.

Meanwhile, when the through-hole 131 of the air discharging part 124 is formed higher than the maximum water level of the cleaning water in the toilet water tank 155, the contaminated air introduced into the air discharging part 124 may be discharged into a space inside the partition 121 through the through-hole 131. In this case, the contaminated air inside the partition 121 is discharged to an external space through the second air passage part 108.

Figure 4:
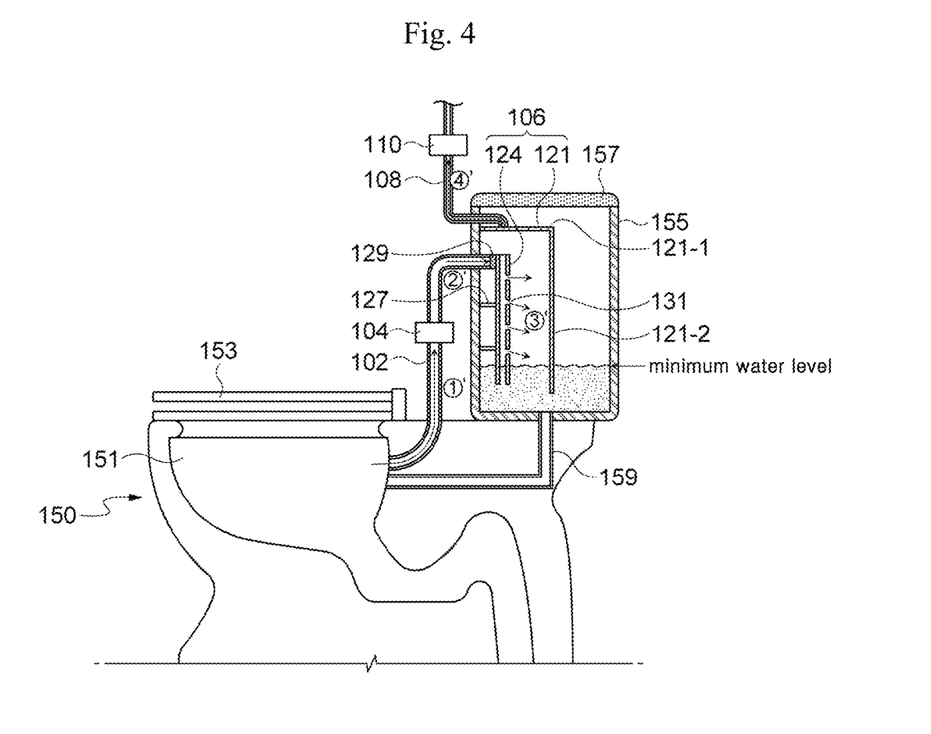
FIG. 4 is a view illustrating a process in which the contaminated air in the toilet hole is discharged to the outside, when the cleaning water in the toilet water tank reaches a minimum water level, in the air treatment device according to one embodiment of the present invention.

FIG. 4 is a view illustrating a process in which the contaminated air in the toilet hole is discharged to the outside, when the cleaning water in the toilet water tank reaches the minimum water level, in the air treatment device according to one embodiment of the present invention.

Referring to FIG. 4, the contaminated air in the toilet hole 151 is introduced into the first air passage part 102 through the first air suction part 104 (①'). Then the contaminated air introduced into the first air passage part 102 flows along the first air passage part 102, and then is introduced into the air discharging part 124 (②'). Here, when the cleaning water in the toilet water tank 155 is located at the minimum water level, the through-hole 131 of the air discharging part 124 is exposed to the air. In this case, the contaminated air introduced into the air discharging part 124 is discharged into the space inside the partition 121 through the through-hole 131 (③'). Since the side plate 121-2 of the partition 121 is formed lower than the minimum water level of the cleaning water in the toilet water tank 155, the contaminated air discharged into the space inside the partition 121 is isolated from the outside. At this time, some of the contaminated air inside the partition 121 may be dissolved in the cleaning water of the toilet water tank 155. The cleaning water of the toilet water tank 155, in which the contaminated air is dissolved, is discharged to the toilet tank (not shown) through operations ④ and ⑤, as illustrated in FIG. 3. Then, the contaminated air inside the partition 121 is introduced into the second air passage part 108 through the second air suction part 110 (④'). And, the contaminated air inside the partition 121 is discharged to the external space through the second air passage part 108 (⑤').

Meanwhile, even when the contaminated air of the external space is introduced through the second air passage part 108, while the second air suction part 110 is not operated, the contaminated air of the external space is isolately maintained in the space inside the partition 121, and thus prevented from being introduced into the bathroom. At this time, the contaminated air of the external space, which exists inside the partition 121, is discharged again to the external space, when the second air suction part 110 is operated.

According to the embodiment of the present invention, the contaminated air in the contamination space may be discharged, while the contaminated air is prevented from being introduced from the external space into an indoor side.

Also, the air treatment device 100 may include a water level control part (not shown) which controls the water level of the cleaning water in the toilet water tank 155. When the plurality of through-holes 131 are formed along the air discharging part 124 from the upper end of the air discharging part 124 to the lower end thereof to be spaced at regular intervals, an amount of the contaminated air which is discharged through the air discharging part 124 may be controlled by controlling the water level of the cleaning water in the toilet water tank 155. For example, when the contamination level in the contamination space is high, all of the through-holes 131 are exposed to the air inside the partition 121 by controlling the water level of the cleaning water in the toilet water tank 155 to be the minimum water level, and thus a large amount of air is discharged to the space inside the partition 121 through the through-hole 131. At this time, the contaminated air inside the partition 121 is discharged to the external space through the second air passage part 108. When a large amount of the contaminated air is discharged to the space inside the partition 121, the suction intensity of the second air suction part 110 may be strengthened, and thus the contaminated air inside the partition 121 may be rapidly introduced into the second air passage part 108. As described above, the contaminated may be discharged to the outside by controlling the water level of the cleaning water in the toilet water tank 155 according to the contamination level in the contamination space. And the contaminated may be rapidly discharged to the outside by controlling the suction intensity of the second air suction part 110 (or the water level of the cleaning water in the toilet water tank 155) according to the amount of the contaminated air discharged to the inside of the partition 121.

Figure 5:
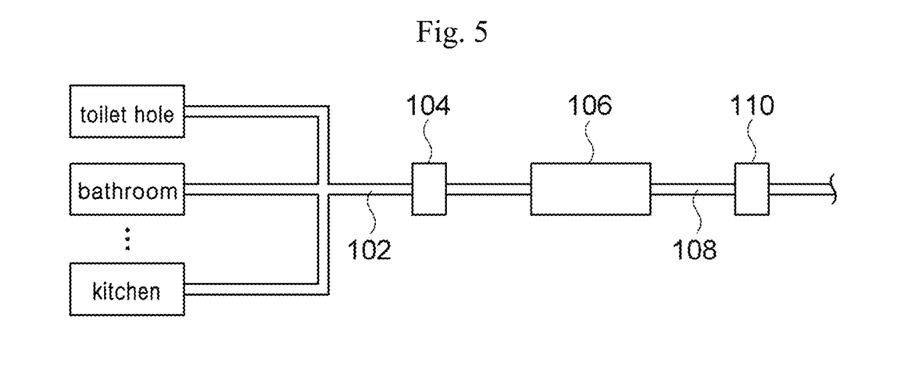
FIG. 5 is a view schematically illustrating an air treatment device according to another embodiment of the present invention.

FIG. 5 is a view schematically illustrating an air treatment device according to another embodiment of the present invention.

Referring to FIG. 5, one side of the first air passage part 102 may be divided into several branches, and then may be connected with each contamination space such as the toilet hole, the bathroom, and a kitchen. In this case, the contaminated air in the contamination space such as the toilet hole, the bathroom, and the kitchen may be introduced into the air treatment part 106 through the first air suction part 104, and then may be discharged to the toilet tank (not shown) or may be discharged to the external space through the second air suction part 104 and the second air passage part 108. Here, the contamination space has been described as the toilet hole, the bathroom, and the kitchen, but the present invention is not limited thereto. Various other spaces (e.g., a living room, a veranda, a garbage storage place, a smoking room, a resting room, an office, a laboratory, a reading room, a place having a lower oxygen concentration than a predetermined reference value, or the like) may be applied.

Figure 6:
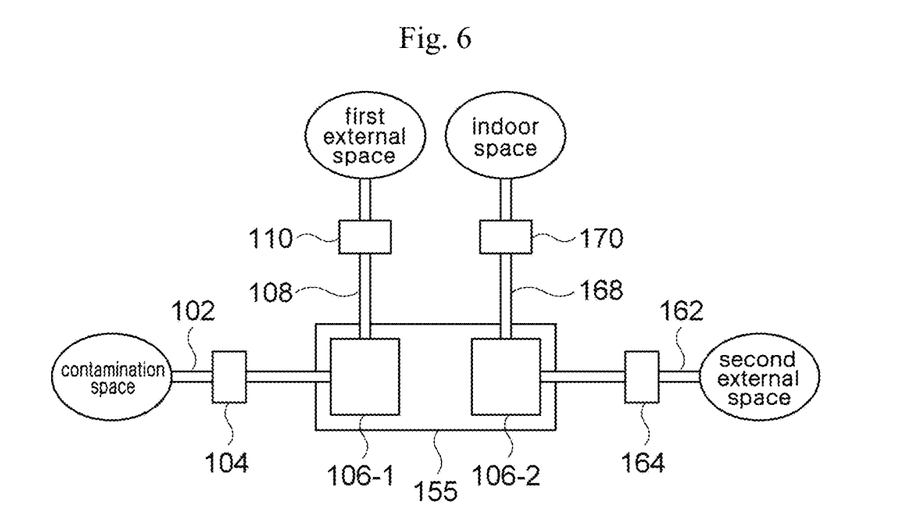
FIG. 6 is a view schematically illustrating an air treatment device according to still another embodiment of the present invention.

FIG. 6 is a view schematically illustrating an air treatment device according to still another embodiment of the present invention.

Referring to FIG. 6, two air treatment parts 106-1 and 106-2 may be formed in the toilet water tank 155 to be spaced from each other. As described above, the first air treatment part 106-1 serves to discharge the contaminated air in the contamination space introduced through the first air passage part 102 and the first air suction part 104 to the toilet tank (not shown), or to discharge the contaminated air to a first external space through the second air passage part 108 and the second air suction part 110.

One side of a third air passage part 162 is connected with the second air treatment part 106-2 (more specifically, an air discharging part of the second air treatment part 106-2), and the other side thereof is connected with a second external space. At this time, the second external space may be a separate space from the first external space, but is not limited thereto. The second external space may be a space outside a building. The third air suction part 164 serves to introduce the air of the second external space into the third air passage part 162. At this time, foreign substances such as yellow sand, a resin powder, and dust may be included in the air in the second external space. When the air of the second external space is introduced, the air of the second external space may be directly introduced, or may be filtered (or purified) and then introduced. That is, the third air suction part 164 may primarily filter the foreign substances (e.g., yellow sand, dust, a resin powder, and pollen) included in the second external space and then may introduce the air into the second air treatment part 106-2. The third air suction part 164 may controls the suction intensity according to a contamination level of the second external space.

One side of a fourth air passage part 168 is connected with the second air treatment part 106-2 (more specifically, a partition of the second air treatment part 106-2), and the other side thereof is connected with an indoor space. Here, the indoor space may be a main room, a study room, a living room, a kitchen, a bathroom, a resting room or the like. A fourth air suction part 170 serves to introduce the air in the second air treatment part 106-2 into the fourth air passage part 168.

Here, when the air in the second external space is introduced into the second air treatment part 106-2 through the third air passage part 162 and the third air suction part 164, the foreign substances (e.g., yellow sand, a resin powder, dust, or the like) contained in the air in the second external space are settled and dissolved in the cleaning water of the toilet water tank 155 in the second air treatment part 106-2. At this time, the cleaning water in which the foreign substances are dissolved is discharged to the toilet tank (not shown) through the toilet hole 151. Then, the air of the second external space, from which the foreign substances are removed, remains in the second air treatment part 106-2. At this time, the fourth air suction part 170 introduces the air of the second external space, from which the foreign substances in the second air treatment part 106-2 are removed, into the fourth air passage part 168, and then discharges the air into the indoor space. In this case, the fresh and clean air is discharged into the indoor space.

The second air treatment part 106-2 serves to purify the air of the second external space including the foreign substances and then to discharge the air into the indoor space. That is, even in the case of the air outside the building (e.g. a countryside which is believed to have clean air), the air often includes the foreign substances such as yellow sand, a resin powder, and dust. When the air containing the foreign substances is directly introduced into the indoor space, it may have an adverse effect on a resident's health. Therefore, since the air of the second external space containing the foreign substances is purified through the second air treatment part 106-2 and then discharged into the indoor space, the resident may have fresh and clean air.

As described above, the contaminated air in the contamination space is discharged into the toilet tank (not shown) or the first external space and then treated by the first air treatment part 106-1, and the foreign substances contained in the air of the second external space are removed by the second air treatment part 106-2, and thus the fresh and clean air may be provided in the indoor space.

Here, it has been described that all of the first and second air treatment parts 106-1 and 106-2 are provided in the toilet water tank 155, but the present invention is not limited thereto. Only one of the first and second air treatment parts 106-1 and 106-2 may be provided in the toilet water tank 155.

Although a few embodiments of the present invention have been shown and described, it would be appreciated by those skilled in the art that changes may be made in these embodiments without departing from the principles and spirit of the invention, the scope of which is defined in the claims and their equivalents.

[Detailed Description of Main Elements]

| | |
|---|---|
| 100: air treatment device | 102: first air passage part |
| 104: first air suction part | 106: air treatment part |
| 108: second air passage part | 110: second air suction part |
| 121: partition | 121-1: upper plate |
| 121-2: side plate | 124: air discharging part |
| 127: fixing part | 129: connection part |
| 131: through-hole | 150: toilet |
| 151: toilet hole | 153: toilet cover |
| 155: toilet water tank | 157: toilet water tank cover |
| 159: connection passage | 162: third air passage part |
| 164: third air suction part | 168: fourth air passage part |
| 170: fourth air suction part | |

The invention claimed is:

1. An air treatment device comprising
a first air passage part of which one side is connected with at least one contamination space;
a first air suction part, comprising at least one of a suction fan and a pump, configured to introduce contaminated air in the at least one contamination space into the first air passage part; and
a first air treatment part formed within a toilet water tank, the first air treatment part connected with the other side of the first air passage part, the first air treatment part comprising:
a partition formed within the toilet water tank, the partition spaced apart from a lower surface of the toilet water tank, the partition having a lower end formed lower than a minimum water level of a cleaning water in the toilet water tank,
wherein the lower end of the partition is submerged in the cleaning water when the cleaning water is at the minimum water level;
there is a gap between the lower end of the partition and the lower surface of the toilet water tank, and the cleaning water in the toilet water tank flows into the inside of the partition through the gap; and
an air inside the partition is isolated by the partition from an air which is inside the toilet water tank and outside the partition when the toilet water tank is filled with the cleaning water; and
an air discharging part vertically formed within an inside of the partition and being in communication with the other side of the first air passage part to discharge the contaminated air into the cleaning water and/or the air in the inside of the partition via a plurality of through-holes formed in the air discharging part in accordance with a level of the cleaning water in the toilet water tank, the plurality of through-holes formed along the air discharging part from an upper end of the air discharging part to a lower end thereof, the plurality of through-holes being in communication with the inside of the partition,
wherein, when the cleaning water reaches a maximum water level, the air discharging part discharges the contaminated air into the cleaning water through the through-holes, thereby allowing the contaminated air to blend into the cleaning water,
wherein, when the cleaning water reaches the minimum water level, the air discharging part discharges the contaminated air into the partition through the through-holes, and
wherein the air treatment device further comprises:
a second air passage part, one side of which is connected to the space inside the partition and the other side of which is connected to a first external space, which is not the contamination space;
a second air suction part which comprises at least one of a suction fan and a pump and is configured to introduce the contaminated air inside the partition into the second air passage part;
a second air treatment part formed in the toilet water tank to be spaced from the first air treatment part;
a third air passage part of which one side is connected with a second external space that is different from the at least one contamination space, and the other side is connected with an air discharging part of the second air treatment part;
a third air suction part, comprising at least one of a suction fan and a pump for introducing the air into the third air passage part, configured to introduce air of the second external space into the third air passage part;
a fourth air passage part of which one side is connected with a partition of the second air treatment part, and the other side is connected with an indoor space; and
a fourth air suction part configured to enable the air inside the partition of the second air treatment part to introduce into the fourth air passage part.

2. The device of claim 1, wherein the water level of cleaning water in the toilet water tank is controlled according to a contamination level in the at least one contamination space.

3. The device of claim 1, wherein the second air suction part controls suction intensity according to an amount of the contaminated air discharged inside the partition or the water level of the cleaning water in the toilet water tank.

4. The device of claim 1, wherein the partition comprises an upper plate formed horizontally in the toilet water tank, one end of the upper plate formed horizontally is fixed to a side wall of the toilet water tank, and a side plate extended downwardly from the other end of the upper plate and, a lower end of the side plate is spaced apart from the lower surface of the toilet water tank.

5. The device of claim 1, wherein the at least one contamination space is at least one of a toilet hole in a toilet, a bathroom, a kitchen, a living room, a veranda, a smoking room, a resting room, a garbage storage place, an office, a laboratory, a reading room, and a place having a lower oxygen concentration than a predetermined reference value.

6. The device of claim 1, wherein the third air suction part filters the air of the second external space introduced through the third air passage part, and then introduces the air into the second air treatment part.

* * * * *